United States Patent [19]

Schloesser et al.

[11] Patent Number: 5,214,146

[45] Date of Patent: May 25, 1993

[54] DERIVATIVES OF QUINOLINECARBOXYLIC ACIDS

[75] Inventors: Ulrike Schloesser, Mannheim; Gerhard Wagenblast, Weisenheim, both of Fed. Rep. of Germany

[73] Assignee: BASF Aktiengesellschaft, Ludwigshafen, Fed. Rep. of Germany

[21] Appl. No.: 775,439

[22] Filed: Oct. 15, 1991

[30] Foreign Application Priority Data

Dec. 10, 1990 [DE] Fed. Rep. of Germany ....... 4039298

[51] Int. Cl.$^5$ ........................................... C07D 215/22
[52] U.S. Cl. ..................................... 546/169; 546/170; 427/146
[58] Field of Search .................................. 546/169, 170

[56] References Cited

FOREIGN PATENT DOCUMENTS 0339518 11/1989 European Pat. Off. .
0384313 8/1990 European Pat. Off. .
 440008 5/1927 Fed. Rep. of Germany .
3405395 8/1984 Fed. Rep. of Germany .

OTHER PUBLICATIONS

Chem. Heterocycl. Comp., vol. 24, 670, 1988 "Synthesis of Quinoline-4-Carboxylic Acid and its Derivatives".

*Primary Examiner*—C. Warren Ivy
*Assistant Examiner*—James H. Turnipseed
*Attorney, Agent, or Firm*—Oblon, Spivak, McClelland, Maier & Neustadt

[57] ABSTRACT

Quinolinecarboxylic acid derivatives of the formula:

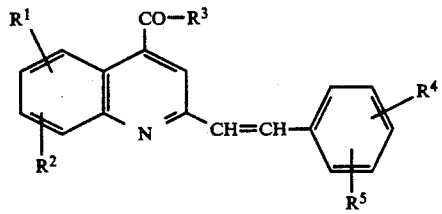

where
 $R^1$ and $R^2$ are identical or different and each is independently of the other hydrogen or halogen,
 $R^3$ is $C_1$-$C_{13}$-alkoxy, $C_1$-$C_8$-monoalkylamino or di($C_1$-$C_8$alkyl)amino and
 $R^4$ and $R^5$ are identical or different and each is independently of the other hydrogen, $C_1$-$C_{13}$-alkyl or $C_1$-$C_{13}$-alkoxy, with the proviso that $R^3$ is not methoxy or ethoxy when at the same time $R^1$, $R^2$, $R^4$ and $R^5$ are each hydrogen, are useful as color formers for preparing pressure-sensitive papers.

3 Claims, No Drawings

DERIVATIVES OF QUINOLINECARBOXYLIC ACIDS

The present invention relates to novel quinolinecarboxylic acid derivatives of the formula I

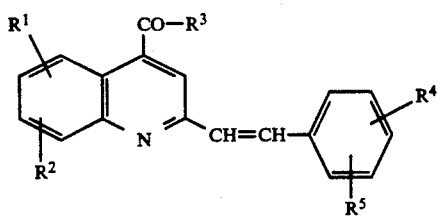

where
$R^1$ and $R^2$ are identical or different and each is independently of the other hydrogen or halogen,
$R^3$ is $C_1$–$C_{13}$-alkoxy, $C_1$–$C_8$-monoalkylamino or di($C_1$–$C_8$-alkyl)amino and
$R^4$ and $R^5$ are identical or different and each is independently of the other hydrogen, $C_1$–$C_{13}$-alkyl or $C_1$–$C_{13}$-alkoxy, with the proviso that $R^3$ is not methoxy or ethoxy when at the same time $R^1$, $R^2$, $R^4$ and $R^5$ are each hydrogen, and to the use of quinolinecarboxylic acid derivatives as color formers for preparing pressure-sensitive recording papers.

DE-A-440 008 discloses the methyl and ethyl esters of 2-styrylquinoline-4-carboxylic acid and uses them as intermediates or starting materials for the preparation of 4-aminoquinoline derivatives which are useful as bactericides. These compounds are also described in Chem. Heterocycl. Comp. Vol. 24 (1988), 670. Nothing is said about use as color former.

DE-A-3 405 395 discloses quinoline-based color formers. These color formers are 2-styrylquinoline derivatives which have no substituents in ring position 4 of the quinoline ring.

Moreover, EP-A-339 518 and EP-A-384 313 describe quinoline derivatives which have a substituted phenyl group in ring position 2 and can be used as color formers. However, it has been found that the prior art products still have application defects.

It is an object of the present invention to provide novel quinolinecarboxylic acid derivatives which have advantageous application properties.

We have found that this object is achieved by the quinolinecarboxylic acid derivatives of the formula I defined at the beginning.

Any alkyl appearing in the abovementioned formula I may be either straight-chain or branched.

$R^1$ and $R^2$ are for example fluorine, chlorine or bromine.

$R^4$ and $R^5$ are for example methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl or isotridecyl. (The terms isooctyl, isononyl, isodecyl and isotridecyl are trivial names derived from the oxo process alcohols (cf. Ullmanns Encyclopädie der technischen Chemie, 4th edition, volume 7, pages 215 to 217, and volume 11, pages 435 and 436.)

$R^4$ and $R^5$ may also be for example, like $R^3$, methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, 2-methylpentyloxy, heptyloxy, octyloxy, 2-ethylhexyloxy, isooctyloxy, nonyloxy, isononyloxy, decyloxy, isodecyloxy, undecyloxy, dodecyloxy, tridecyloxy or isotridecyloxy.

$R^3$ may also be for example mono- or dimethylamino, mono- or dimethylamino, mono- or dipropylamino, mono- or diisopropylamino, mono- or dibutylamino, mono- or diisobutylamino, mono- or di(sec-butyl)amino, mono- or dipentylamino, mono- or diisopentylamino, mono- or dineopentylamino, mono- or dihexylamino, mono- or diheptylamino, mono- or dioctylamino, mono- or diisooctylamino, mono- or di(2-ethylhexyl)amino, mono- or dinonylamino, mono- or diisononylamino, mono- or didecylamino, mono- or diisodecylamino, mono- or diundecylamino, mono- or didodecylamino, mono- or ditridecylamino or mono- or diisotridecylamino.

Preference is given to quinolinecarboxylic acid derivatives of the formula I where
$R^1$ and $R^2$ are each independently of the other hydrogen or chlorine,
$R^3$ is $C_1$–$C_8$-alkoxy, $C_1$–$C_4$-monoalkylamino or di($C_1$–$C_4$-alkyl)amino, and
$R^4$ and $R^5$ are each independently of the other hydrogen or $C_1$–$C_4$-alkoxy.

Particular preference is given to quinolinecarboxylic acid derivatives of the formula I where
$R^1$ and $R^2$ are each hydrogen,
$R^3$ is $C_1$–$C_8$-alkoxy, $C_1$–$C_4$-monoalkylamino or di($C_1$–$C_4$-alkyl)amino and
$R^4$ and $R^5$ are each independently of the other $C_1$–$C_4$-alkoxy, or one of $R^4$ and $R^5$ may also be hydrogen.

The novel quinoline derivatives of the formula I can be obtained in a conventional manner, for example as described in Chem. Heterocycl. Comp. Vol. 24 (1988), 670.

For example, isatins of the formula II

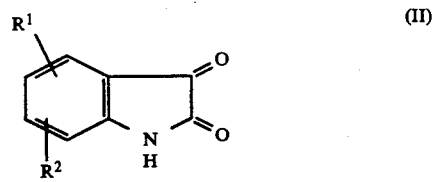

Where $R^1$ and $R^2$ are each as defined above, can be converted with acetone in the presence of a base in 2-methylquinolinecarboxylic acids of the formula III

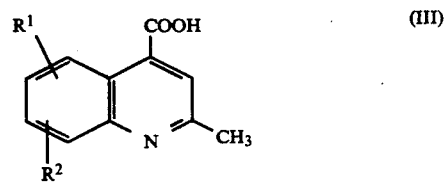

where $R^1$ and $R^2$ are each as defined above.

By condensing benzaldehydes of the formula IV

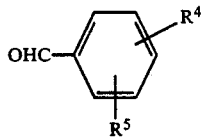

where R[4] and R[5] are each as defined above, with the methylquinolinecarboxylic acids III in an acid medium it is possible to arrive at the styrylquinolinecarboxylic acids of the formula V

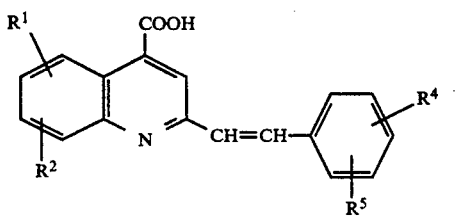

where R[1], R[2], R[4] and R[5] are each as defined above. They can then be for example converted into the corresponding carbonyl halides and reacted with compounds of the formula VI

where R[3] is as defined above, to give the quinolinecarboxylic acid derivatives of the formula I.

The present invention further provides for the use of quinolinecarboxylic acid derivatives of the formula Ia

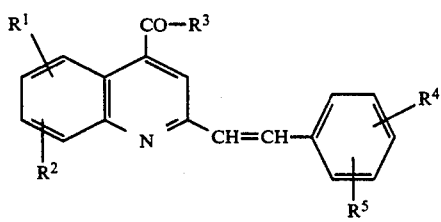

where
R[1] and R[2] are identical or different and each is independently of the other hydrogen or halogen,
R[3] is $C_1$–$C_{13}$-alkoxy, $C_1$–$C_8$-monoalkylamino or di($C_1$–$C_8$-alkyl)amino and
R[4] and R[5] are identical or different and each is independently of the other hydrogen, $C_1$–$C_{13}$-alkyl or $C_1$–$C_{13}$-alkoxy,
as a color former for preparing pressure-sensitive recording papers.

The quinolinecarboxylic acid derivatives of the formula Ia are slightly colored or colorless compounds whose solutions in inert organic solvents produce on contact with electron acceptors colorings in greenish yellow to reddish orange shades, depending on the substitution pattern of the quinolinecarboxylic acid derivative. Examples of electron acceptor substances are carboxylic or mineral acids, kaolin, bentonite, activated clay, aluminum silicate, attapulgite or any other desired clay, acidic polymeric materials, such as condensation products based on phenols and/or phenolsulfonic acids, also metal oxides or salts, such as zinc oxide, aluminum oxide, zinc chloride, iron stearate or cobalt naphthenate.

Owing to these properties, the compounds of the formula Ia are suitable for use as color formers in pressure-sensitive recording materials.

For use in pressure-sensitive systems, the quinolinecarboxylic acid derivatives Ia are advantageously microencapsulated in the form of solutions in organic solvents, for example chloroparaffins, partially hydrogenated biphenyl or terphenyl, alkylbenzenes, alkylnaphthalenes, alkylated dibenzylbenzenes, paraffin oil, mineral oil or else customary low-boiling solvents, such as xylene or toluene, and applied in microencapsulated form to the base material, for example paper. On the application of pressure, contact with electron acceptors will then result in color formation in the area where the pressure was applied.

Suitable processes for preparing microcapsules are known for example from US-A-2 800 457, US-A-2 800 458, DE-A-2 119 933 or EP-A-26 914. It is also possible to disperse the compounds of the present invention by the process described in US-A-3 103 404 in wax or oil-wax mixtures and to use these mixtures to coat base materials, such as foils or paper. Pressure-sensitive materials are obtained which are suitable for copying onto electron acceptor coated substances and which after use are removed like carbon paper.

The Examples which follow will further illustrate the invention.

EXAMPLE 1

Stage 1: 2-Methylquinoline-4-carboxylic acid 287 g (1.6 mol) of moist isatin (dry matter content: 82% by weight) were suspended in 2000 ml of 38% strength by weight sodium hydroxide solution, admixed with 25.4 g (0.64 mol) of sodium hydroxide and 1.1 g of wetting agent, and heated to 50° C. At that temperature 93 g (1.6 mol) acetone were added over 15 minutes. The mixture was subsequently stirred at 50° C. for 3 hours and then cooled down to 25° C, and the solid product was filtered off with suction. After washing with 33% strength by weight sodium hydroxide solution the residue was dissolved in 2.5 l of water, reprecipitated with 30% strength by weight hydrochloric acid at pH 2, filtered off with suction and washed with water acidified with hydrochloric acid (pH 2).

Drying at 60° C. left 219 g (73%) of 2-methyl-quinoline-4-carboxylic acid of melting point 247-249° C. Stage 2: 2-(4-Methoxystyryl)quinoline-4-carboxylic acid 150 g (0.8 mol) of 2-methylquinoline-4-carboxylic acid and 110 g (0.8 mol) of p-methoxybenzaldehyde were heated at the boil in 300 ml of glacial acetic acid for 6 hours during which 73 g of glacial acetic acid were distilled off at the same time. The carboxylic acid was isolated and purified by filtering off with suction and washing with glacial acetic acid and methanol. Drying left 144 g (59%) of 2-(4-methoxystyryl)quinoline-4-carboxylic acid of melting point 284-286° C. Stage 3: Methyl 2-(4-methoxystyryl)quinoline-4-carboxylate 12.3 g (0.04 mol) of 2-(4-methoxystyryl)quinoline-4-carboxylic acid in 50 ml of thionyl chloride and 1 ml of pyridine were heated at 30° C. for 90 minutes and then at 60° C. for a further 15 minutes. The excess thionyl chloride was removed under reduced pressure, and the acid chloride was converted with 150 ml of methanol into the methyl ester of 2-(4-methoxystyryl)quinoline-4-carboxylic acid. After standing at room temperature for 12 hours, the product, which had precipitated in the form of a hydrochloride, was filtered off with suction and washed with methanol. The base was liberated by suspending and stirring the crude product in aqueous bicarbonate solution until the initially red material turned yellow.

The yield of methyl 2-(4-methoxystyryl)quinoline-4-carboxylate of the formula

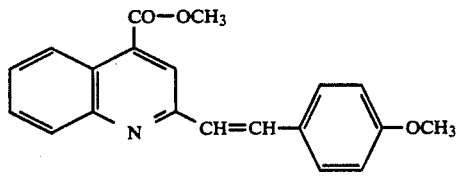

after filtering off with suction while washing until neutral and drying was 7.2 g (56%).

Melting point 99.5° C.

$\lambda_{max}$(measured in dichloromethane): 373 nm.

$\lambda_{max}$(measured in methanol, containing 2% by weight of hydrogen chloride): 432 nm.

EXAMPLE 2

2-(4-Methoxystyryl)quinoline-4-N,N-di-n-butylcarboxamide 12.3 g (0.04 mol) of 2-(4-methoxystyryl)quinoline-4-carboxylic acid (see Example 1) were dissolved in 50 ml of thionyl chloride by stirring at not more than 30° C. and admixed with 1 ml of pyridine. After 1.75 hours the excess thionyl chloride was removed under reduced pressure and the residue was admixed with 150 ml of di-n-butylamine while cooling with ice, and the reaction temperature rose to 80° C. The reaction mixture was stirred at room temperature for a further 12 hours and was then poured into 500 ml of water. The organic phase was purified by stirring out with 5% strength by weight hydrochloric acid and filtering the resulting residue off with suction. For further purification, the residue was taken up in toluene and then washed with 5% strength by weight hydrochloric acid and dilute sodium hydroxide solution.

The oil resulting on drying over sodium sulfate and removing the solvent was purified by filtration through silica gel with 4:1 (v/v) toluene/ethyl acetate. Crystallization with cyclohexane gave 4.6 g (27%) of 2-(4-methoxystyryl)quinoline-4-N,N-di-n-butylcarboxamide of the formula

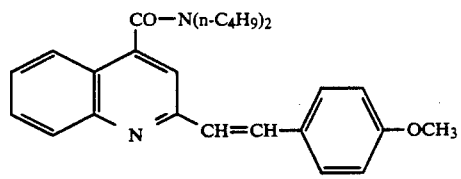

of melting point 77° C.

$\lambda_{max}$ (measured in dichloromethane): 362 nm.

$\lambda_{max}$ (measured in methanol, containing 2% by weight of hydrogen chloride): 420 nm.

The procedures described in Examples 1 and 2 were also used to obtained the quinolines of the formula

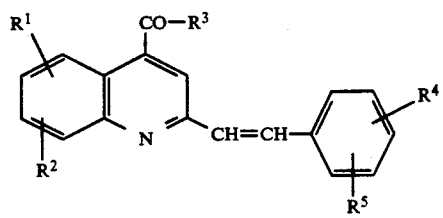

listed in the following Table:

TABLE

| No. | $R^1$ | $R^2$ | $R^3$ | $R^4$ | $R^5$ | m.p. [°C.] | λ max*) [nm] | λ max**) [nm] |
|---|---|---|---|---|---|---|---|---|
| 3 | H | H | OCH$_3$ | 3-OCH$_3$ | 4-OCH$_3$ | 133 | 377 | 445 |
| 4 | H | H | N(C$_4$H$_9$)$_2$ | 3-OCH$_3$ | 4-OCH$_3$ | öl | 367 | 432 |
| 5 | H | H | OCH$_3$ | H | 4-CH$_3$ | 119 | 364 | 408 |
| 6 | 4-Cl | 4-Cl | OCH$_3$ | H | 4-OCH$_3$ | 156 | 365 | 407 |
| 7 | H | H | O—nC$_4$H$_9$ | H | 4-OCH$_3$ | 90 | 372 | 432 |
| 8 | H | H | O—nC$_4$H$_9$ | H | H | 42 | 359 | 395 |
| 9 | H | H | O—nC$_4$H$_9$ | H | 4-nOC$_4$H$_9$ | 81 | 374 | 436 |
| 10 | H | H | O—nC$_8$H$_{17}$ | H | 4-OCH$_3$ | 59 | 372 | 432 |
| 11 | H | H | O—nC$_4$H$_9$ | H | 2-nOC$_4$H$_9$ | 56 | 367 | 424 |
| 12 | H | H | N—nC$_8$H$_{17}$ | H | 4-OCH$_3$ | 131 | 377 | 415 |
| 13 | H | H | O—nC$_4$H$_9$ | 3-OCH$_3$ | 4-OCH$_3$ | 111 | 379 | 439 |
| 14 | H | H | O—nC$_6$H$_{13}$ | 3-OCH$_3$ | 4-OCH$_3$ | 105 | 381 | 435 |
| 15 | H | H | O—nC$_8$H$_{17}$ | 3-OCH$_3$ | 4-OCH$_3$ | 101 | 392 | 439 |
| 16 | H | H | N—nC$_8$H$_{17}$ | 3-OCH$_3$ | 4-OCH$_3$ | 151 | 385 | 430 |
| 17 | H | H | O—CH$_3$ | 2-OCH$_3$ | 4-OCH$_3$ | 130 | 372 | 438 |

*)measured in dichloromethane
**)measured in methanol containing 2% by weight of hydrogen chloride

EXAMPLE 18

(Use)

A 0.5% strength by weight solution of the quinolinecarboxylic acid derivative of Example 3 in diisopropylnaphthalene was applied with a 6 μm draw bar to a CF paper from wiggins Teape. A yellow color developed, whose K/S value (color strength) was determined by the CIELAB system. After one hour's exposure in the Suntest instrument from Hanau, the ΔE value (light fastness) was determined, again in accordance with CIELAB.

K/S: 2,0, ΔE: 6.

EXAMPLE 19

(Use)

Example 18 was repeated with the quinolinecarboxylic acid derivative of Example 1.

K/S: 2.4, ΔE: 8.

We claim:

1. A quinolinecarboxylic acid derivative of the formula I

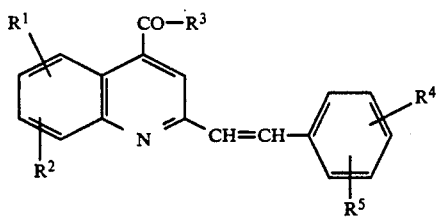

(I)

where
- $R^1$ and $R^2$ are identical or different and each is independently of the other hydrogen or halogen,
- $R^3$ is $C_1$-$C_{13}$-alkoxy, $C_1$-$C_{13}$-monoalkylamino or di($C_1$-$C_8$-alkyl)amino and
- $R^4$ and $R^5$ are identical or different and each is independently of the other hydrogen, $C_1$-$C_{13}$-alkyl or $C_1$-$C_{13}$-alkoxy, with the proviso that $R^3$ is not methoxy or ethoxy when at the same time $R^1$, $R^2$, $R^4$ and $R^5$ are each hydrogen.

2. A quinolinecarboxylic acid derivative as claimed in claim 1, wherein
- $R^1$ and $R^2$ are each independently of the other hydrogen or chlorine,
- $R^3$ is $C_1$-$C_{13}$-alkoxy, $C_1$-$C_4$-monoalkylamino or di($C_1$-$C_4$-alkyl)amino, and
- $R^4$ and $R^5$ are each independently of the other hydrogen or $C_1$-$C_4$-alkoxy.

3. A quinolinecarboxylic acid derivative of the formula I

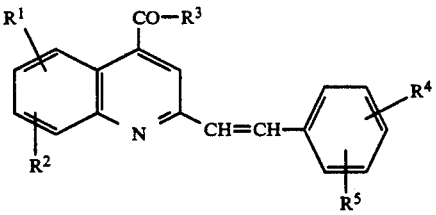

where
- $R^1$ and $R^2$ are identical or different and each is independently of the other hydrogen or halogen,
- $R^3$ is $C_1$-$C_{13}$-alkoxy, $C_1$-$C_8$-monoalkylamino or di($C_1$-$C_8$-alkyl)amino and
- $R^4$ and $R^5$ are identical or different and each is independently of the other hydrogen or $C_1$-$C_{13}$-alkoxy, with the proviso that either $R^4$ or $R^5$ must be $C_1$-$C_{13}$-alkoxy.

* * * * *